(12) United States Patent
Huthmacher

(10) Patent No.: US 11,840,420 B2
(45) Date of Patent: *Dec. 12, 2023

(54) METHOD AND DEVICE FOR MONITORING A YARN TENSION OF A RUNNING YARN

(71) Applicant: Oerlikon Textile GmbH & Co. KG, Remscheid (DE)

(72) Inventor: Jörg Huthmacher, Marl (DE)

(73) Assignee: Oerlikon Textile GmbH & Co. KG, Remscheid (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/704,311

(22) Filed: Mar. 25, 2022

(65) Prior Publication Data

US 2022/0212890 A1 Jul. 7, 2022

Related U.S. Application Data

(63) Continuation of application No. 16/617,395, filed as application No. PCT/EP2018/064413 on Jun. 1, 2018, now Pat. No. 11,305,960.

(30) Foreign Application Priority Data

Jun. 7, 2017 (DE) ............... 10 2017 005 450.9
Jul. 7, 2017 (DE) ............... 10 2017 006 431.8

(51) Int. Cl.
*B65H 59/40* (2006.01)
*B65H 63/02* (2006.01)
*G01L 5/102* (2020.01)
*G05B 23/02* (2006.01)
*G01N 33/36* (2006.01)

(52) U.S. Cl.
CPC ............. *B65H 59/40* (2013.01); *B65H 63/02* (2013.01); *G01L 5/102* (2013.01); *G05B 23/0229* (2013.01); *B65H 2701/31* (2013.01); *G01N 33/365* (2013.01)

(58) Field of Classification Search
CPC .... B65H 59/40; B65H 63/02; B65H 2701/31; G05B 23/0229; G01L 5/102; G01N 33/365
See application file for complete search history.

(56) References Cited

U.S. PATENT DOCUMENTS 5,682,146 A 10/1997 Neumann

FOREIGN PATENT DOCUMENTS

| DE | 19614027 | 1/1998 |
| EP | 2107027 | 10/2009 |
| EP | 2644551 | 10/2013 |
| WO | 20150052624 | 4/2015 |

*Primary Examiner* — William E Dondero
(74) *Attorney, Agent, or Firm* — BainwoodHuang

(57) ABSTRACT

Techniques are directed to a method and a device for monitoring a yarn tension of a running yarn in a yarn treatment process. To this end, the yarn tension of the yarn is continuously measured and the measurement signals for the yarn tension are compared with a threshold value of an admissible yarn tension. In the event of an inadmissible tolerance deviation of the measurement signals, a short-term signal path of the yarn tension is detected as a fault graph. In order to enable a fault diagnosis, the fault graph of the yarn tension is analyzed using a machine learning program. The fault graph is then allocated to one of the existing fault categories or to a new fault category. A device for this purpose may include a diagnosis unit, which cooperates accordingly with the yarn tension evaluation unit.

17 Claims, 4 Drawing Sheets

Figure 1:
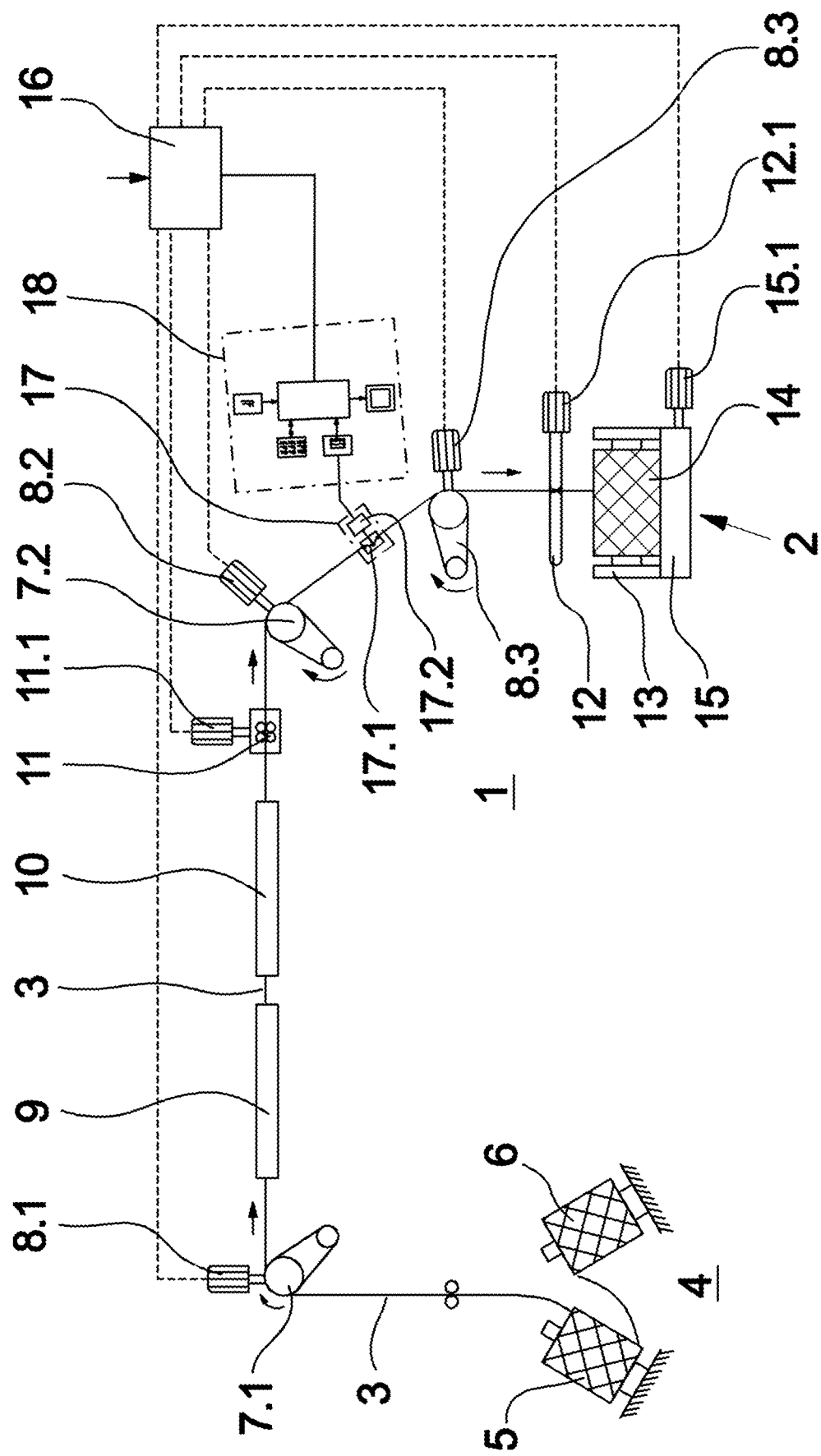

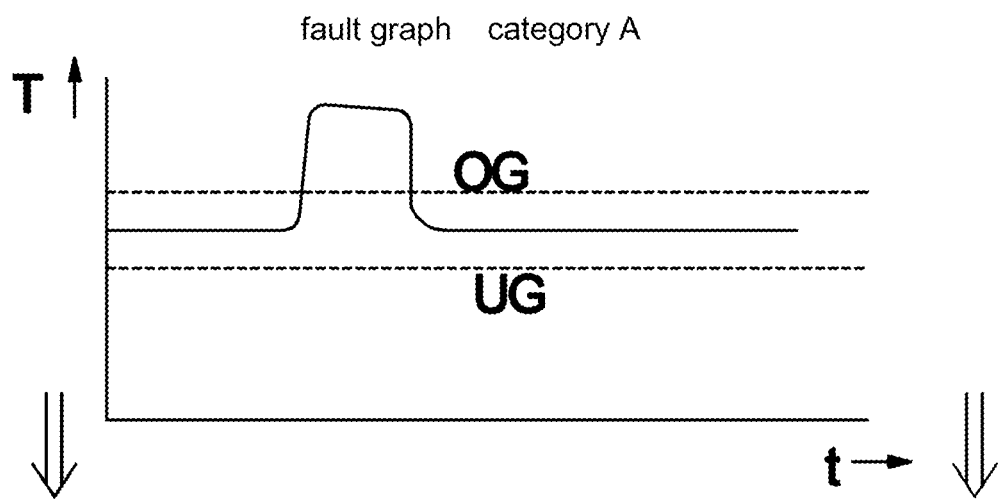
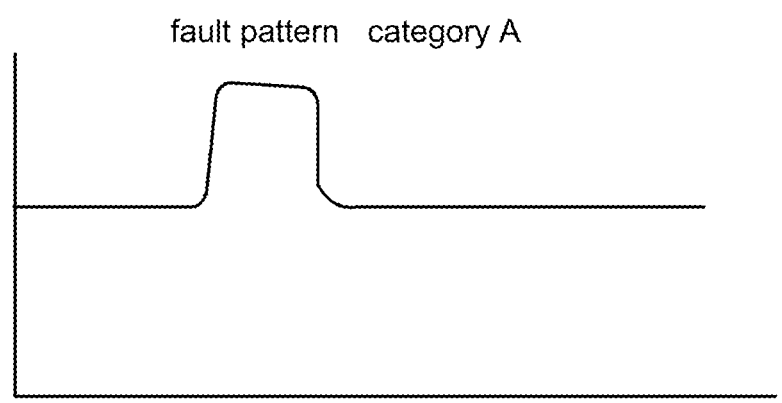
Fig.3.1
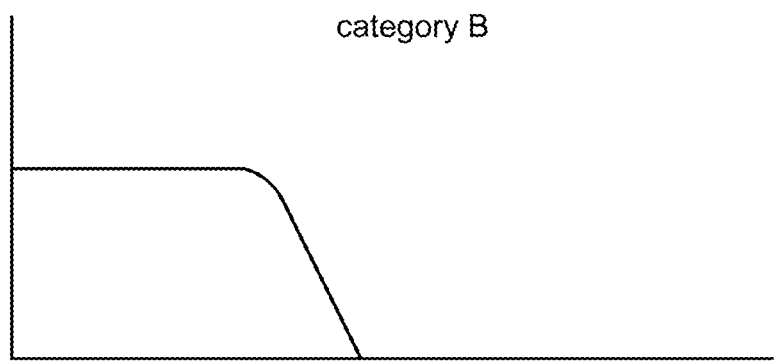
Fig.3.2

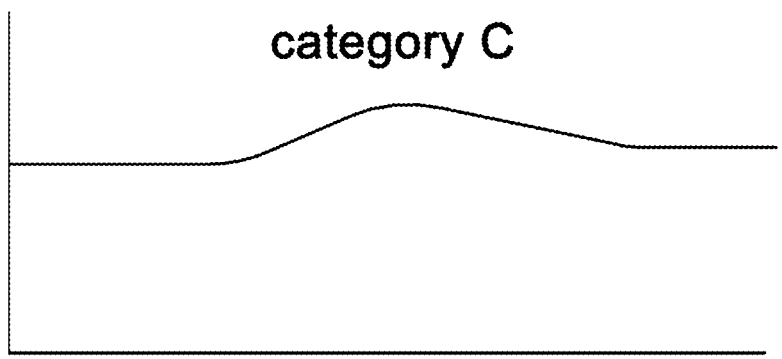
Fig.3.3
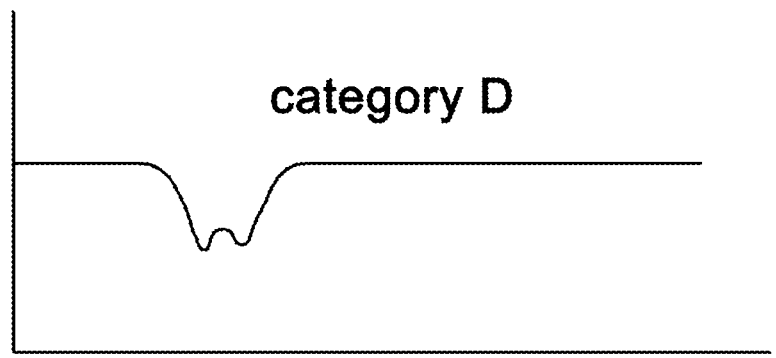
Fig.3.4
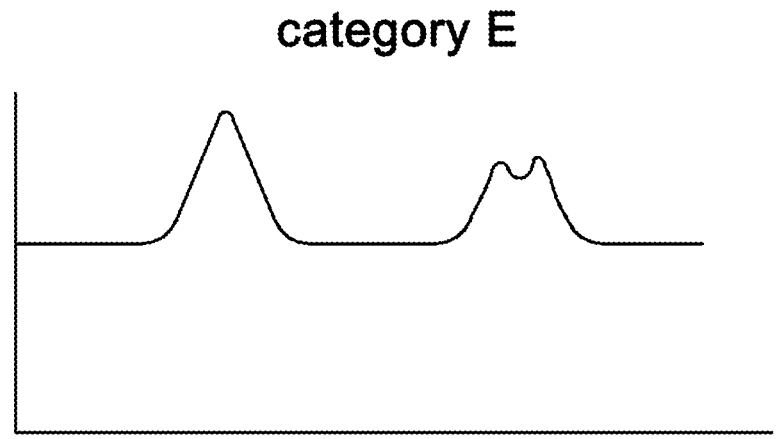
Fig.3.5

METHOD AND DEVICE FOR MONITORING A YARN TENSION OF A RUNNING YARN

This is a continuation patent application of earlier-filed U.S. application Ser. No. 16/617,395, filed on Nov. 26, 2019, and entitled "METHOD AND DEVICE FOR MONITORING A YARN TENSION OF A RUNNING YARN", the contents and teachings of which are hereby incorporated by reference in their entirety.

The invention relates to a method for monitoring a yarn tension of a running yarn in a yarn treatment process and to a device for monitoring as disclosed herein.

A generic method and a generic device for monitoring a yarn tension of a running yarn in a yarn treatment process are known, for example, from DE 196 14 027 A1.

In the production and treatment of yarns, product and/or process parameters are typically continuously monitored to thus obtain the most stable possible process control and in particular the most stable possible product quality of the yarn. In particular in the production of textured yarns, monitoring a yarn tension of the running yarn has proven itself to recognize process disturbances and/or product variations. In the known method and the known device for monitoring a yarn tension of a running yarn, the yarn tension on the yarn is progressively measured for this purpose. The measurement signals of the yarn tension generated in this case are compared to a threshold value of a permissible yarn tension. In this case, so-called fault graphs can be generated, which display the signal curve of the measurement signals of the yarn tension in the event of impermissible tolerance deviation. In particular, quality variations of the yarn may thus be established, which enable a quality classification, for example. In addition, it is known that the fault graphs reflect different signal curves of the yarn tension in dependence on the respective disturbance in the process. Experienced operators can thus use the signal curve of the yarn tension of a fault graph to identify a possible source of disturbance.

It is the object of the invention to refine the generic method and the generic device for monitoring a yarn tension of a running yarn in a yarn treatment process in such a manner that improved process control for producing uniform yarn qualities becomes possible.

A further goal of the invention is to provide a generic method and a generic device for monitoring a yarn tension of a running yarn in a yarn treatment process, using which it is possible to identify process disturbances and also remedy them rapidly and in a targeted manner.

This object may be achieved by a method having features and by a device having features disclosed herein.

Advantageous refinements of the invention are defined by features and feature combinations disclosed herein.

The invention is based on the finding that the fault graphs of the measurement signal curves of the yarn tension can be used as an indication of a process disturbance. To use the fault graphs as the foundation of a diagnosis, according to the invention the fault graph is analyzed using a machine learning program. The fault graph is then assigned to a known fault graph category or a new fault graph category. A unique classification of the fault graph is thus provided. In particular the assignment to a known fault graph category enables an early error diagnosis, so that fundamental disturbance causes are rapidly recognized. Alternatively, however, it is also possible that during the process, previously unknown or previously unconsidered new process disturbances result. In this case, the fault graph can be assigned to a new fault graph category by the machine learning program.

The ascertained fault graphs can be stored to expand a data pool.

Since the fault graphs differ in the curve profile thereof, the option also exists of specifying the fault graph categories by way of a fault pattern of one of the fault graphs or a group of fault graphs of the yarn tension. A visualization of the relevant fault graph category may thus be substantially improved during the analysis of the fault graphs by the machine learning program.

To carry out a rapid and targeted process change after the assignment of the fault graphs to one of the fault graph categories, the method variant is particularly advantageous in which a specific process disturbance and/or a specific operating fault and/or a specific disturbance parameter and/or a specific product fault is/are assigned to each of the fault graph categories. After assignment of the fault graphs, the fundamental cause of the yarn tension deviation can thus be remedied immediately. Large discard quantities may thus be avoided in particular during the production of the yarns.

To automate the respective yarn treatment process, the method variant is advantageous in which after assignment of one of the fault graphs to one of the fault graph categories, a control command relevant to the fault graph category is triggered for a process change. The process change could, for example, effectuate a direct intervention into the yarn treatment process or initiate an intervention by an operator.

Since a plurality of fault graphs occur in a yarn treatment process, the method variant has proven itself in particular in which the analysis of the fault graphs is executed by at least one machine learning algorithm of the machine learning program. An artificial intelligence may thus be used to carry out structured analyses even with a large quantity of data and to find known and new fault graph categories rapidly.

For this purpose, however, it is firstly necessary for the machine learning algorithm to first access ascertained basic data for learning. For this purpose, fault graphs, which have previously been associated with one of the fault graph categories, are transferred to the machine learning algorithm for learning.

After a learning phase, it is possible that the machine learning algorithm, by way of analysis of a predetermined fault graph, independently assigns it to at least one of the existing fault graph categories or a new fault graph category. New causes of disturbances in the process can thus advantageously also be recognized and defined in future.

The device according to the invention permits the yarn tension analysis unit to interact directly with a diagnostic unit, so that error identification and diagnosis become possible. The diagnostic unit thus firstly enables an analysis of a fault graph using a machine learning program and a subsequent assignment of the fault graph to an existing fault graph category or a new fault graph category.

To be able to use the newly ascertained fault graphs for subsequent analyses, the diagnostic unit comprises a storage unit for storing the fault graphs and a programmable learning processor for executing the machine learning program and subsequently determining the fault category.

In this case, the learning processor could be coupled to an input unit, by which one or more ascertained fault graphs can be input. Already known fault graph categories can thus advantageously also be given to the diagnostic unit to improve the machine learning program.

In order that an operator is informed about the respective process run during the process control, it is furthermore provided that the learning processor is coupled to an output unit, by which an assignment of the analyzed fault graphs to one of the fault graph categories can be visualized. This output unit can advantageously be wirelessly coupled to the learning processor in this case and can represent any type of device using which the display of a fault graph category is possible.

To obtain a possibly autonomous system for fault diagnosis, it is furthermore provided that the learning processor comprises a neural network for executing a machine learning program. Complex yarn treatment processes correspondingly having a large variety of data can thus also be monitored continuously and reliably.

To monitor multiple yarn treatment processes, the device according to the invention is advantageously usable in the refinement in which the learning processor is arranged spatially separate from the input unit and the output unit. The option exists in this case that the learning processor is in contact with multiple input units and/or multiple output units. The connection is then preferably established wirelessly, so that the learning processor could also be formed in a virtual space.

The device variant according to the invention is advantageously used for automation in which the diagnostic unit is connected to a machine control unit, by which a control command for the process change is executable. Precise disturbance causes can thus be eliminated immediately after assignment of the respective fault graph.

The method according to the invention for monitoring a yarn tension of a running in a yarn treatment process is explained in greater detail hereafter on the basis of an exemplary embodiment of the device according to the invention with reference to the appended figures.

IN THE FIGURES

Figure 2:
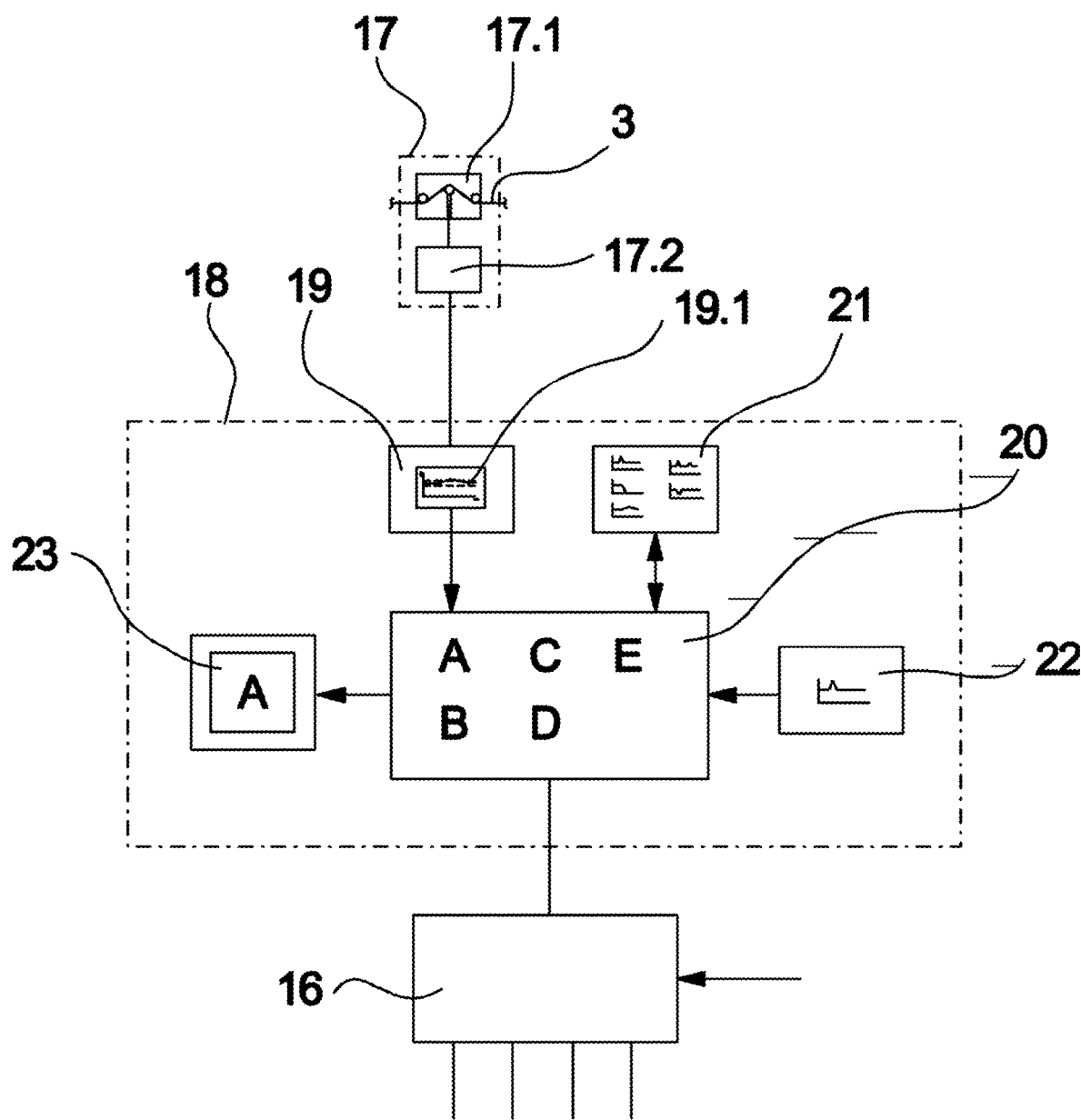

FIG. 1 schematically shows a yarn treatment process having an exemplary embodiment of the device according to the invention for monitoring a yarn tension FIG. 2 schematically shows the exemplary embodiment of the device according to the invention for monitoring a yarn tension from FIG. 1

FIG. 3.1 to FIG. 3.5 show multiple different fault graphs of different fault graph categories FIG. 1 schematically shows a yarn treatment process having an exemplary embodiment of the device according to the invention. The yarn treatment process relates to a texturing process as is executable in a plurality of processing points of a texturing machine. A processing point 1 and a bobbin point 2 of such a texturing machine are schematically shown in FIG. 1. The processing point 1 comprises a feed station 4, in which a feed bobbin 5 and a reserve bobbin 6 are held. The feed bobbin 5 supplies a yarn 3, which is transferred for stretching and texturing into the processing point 1.

The withdrawal of the yarn from the feed bobbin 5 is performed by a first godet unit 7.1. The godet unit 7.1 is driven via a godet drive 8.1. In the further course, a heating unit 9, a cooling unit 10, and a texturing assembly 11 are arranged downstream of the godet unit 7.1. The texturing assembly 11 is driven via a texturing drive 11.1. The texturing assembly 11 is preferably designed as a friction twist generator to generate a false twist on the yarn 3.

A second godet unit 7.2, which is operated by the godet drive 8.2, for stretching the yarn is arranged downstream of the texturing assembly 11. The godet unit 7.2 is identical in construction to the first godet unit 7.1, wherein the second godet unit 7.2 is operated at a higher peripheral velocity to stretch the yarn. The yarn 3 is thus textured and simultaneously stretched inside the processing point 1. After the treatment of the yarn, it is guided through a third godet unit 7.3 to a bobbin point 2. The godet unit 7.3 is driven by the godet drive 8.3.

The bobbin point 2 comprises a bobbin holder 13, which supports a bobbin 14. The bobbin holder 13 is designed as pivotable and may be operated manually or automatically to change the bobbin 14. A drive roller 15, which is driven by a roller drive 15.1, is associated with the bobbin holder 13. A traversing unit 12, which comprises a drivable traversing yarn guide, is associated with the bobbin point 2 for laying the yarn on the circumference of the bobbin 15. The traversing yarn guide is driven for this purpose via the traversing drive 12.1.

The traversing drive 12.1 and the roller drive 15.1 of the bobbin point 2 are formed as individual drives and are connected to a machine control unit 16. The godet drives 8.1, 8.2, and 8.3 and also the texturing drive 11.1 of the processing point 1 are also embodied as individual drives and are coupled to the machine control unit 16.

For the process monitoring, a yarn tension is continuously measured and monitored of the running yarn 3 in a yarn section between the godet units 7.2 and 7.3. For this purpose, a yarn tension measuring unit 17 is provided, which comprises a yarn tension sensor 17.1 and a measurement signal pickup 17.2. The yarn tension measuring unit 17 is connected to a diagnostic unit 18. In addition, reference is made to FIG. 2 for the further explanation of the diagnostic unit 18.

The device according to the invention for monitoring a yarn tension of a running yarn is schematically illustrated in FIG. 2. The diagnostic unit 18 comprises in this case the yarn tension analysis unit 19, which is directly connected to the yarn tension measuring unit 17. The measurement signals of the measurement signal pickup 17.2 are thus supplied to the yarn tension analysis unit 19. The measurement signals are prepared and compared to at least one limiting value inside the yarn tension analysis unit 19. The measurement signal on the yarn tension is typically compared to an upper limiting value and a lower limiting value. As soon as an impermissible tolerance deviation of the yarn tension is recognized, a short-term measurement signal profile of the yarn tension is recorded and generated as a fault graph. For this purpose, the yarn tension analysis unit 19 comprises a fault graph generator 19.1. The fault graph is transferred to a learning processor 20. The learning processor 20 is embodied as programmable and preferably comprises a neural network to execute a machine learning program. The machine learning program comprises at least one machine learning algorithm to be able to carry out extensive analyses using artificial intelligence.

A storage unit 21, in which a data pool of fault graphs is stored, is associated with the learning processor 20. Furthermore, an input unit 22 and an output unit 23 are associated with the learning processor 20.

The connections between the learning processor 20 and the yarn tension measuring unit 17, the storage unit 21, the input unit 22, and the output unit 23 can each be established by a wired or wireless connection. In particular in the case of a wireless connection, the option exists that the individual units do not necessarily have to be kept at the same location. The learning processor 20 is thus preferably wirelessly integrated into the diagnostic unit 18. The option also exists in this case of arranging the learning processor 20 in a virtual space independently of the input unit 22 and the output unit.

The fault graph generated by the fault graph generator 19.1 is analyzed using the machine learning program in the learning processor 20. For this purpose, the machine learning program comprises at least one machine learning algorithm, which executes a structured analysis of the fault graph to identify a fault graph category with the aid of a neural network. A fault graph category can be specified in this case by a single fault pattern of one of the fault graphs or a group of fault graphs.

Several exemplary embodiments of fault patterns of typical fault graphs and fault graph categories are illustrated in FIGS. 3.1 to 3.5. Each of the fault patterns illustrated in FIGS. 3.1 to 3.5 depicts a fault graph which is associated with a specific fault graph category.

In FIG. 3.1, the course of the measurement signal of the yarn tension is illustrated as a fault graph by way of example for this purpose in the upper half of the image. The measurement signal of the yarn tension is compared in this case to an upper limiting value and a lower limiting value. In the fault graph, the upper limiting value is identified by the identifying letters OG and the lower limiting value by the letters UG. For this purpose, the yarn tension T is plotted on the ordinate and the time t is plotted on the abscissa. In the signal profile of the yarn tension illustrated in FIG. 3.1, short-term exceeding of the upper limiting value can be recognized. This very sudden exceeding has its cause in a so-called knot overflow. It can thus be seen from the exemplary embodiment according to FIG. 1 that one end of the feed bobbin is knotted with a beginning of the reserve bobbin to enable a continuous process. This connecting knot in the yarn run results in a short-term yarn tension elevation at the yarn tension sensor 17.1. In particular for the further processing process, the information is of great significance as to whether an end bobbin contains a knot and thus the feed material of two feed bobbins.

In FIG. 3.1, the fault graph illustrated in the upper half of the image is illustrated as a fault pattern in the lower half of the image. The fault pattern illustrated in FIG. 3.1 in the lower half of the image could represent, for example, a fault graph category A. In the later process control, the fault graph category A may thus be ascertained by analysis of the fault graphs and may possibly be visualized with respect to an operator with the fault pattern.

Further fault patterns are illustrated in FIGS. 3.2 to 3.5, which each define a specific fault graph category.

The fault pattern illustrated in FIG. 3.2 defines the fault graph category B. The fault category B could have its disturbance cause in a yarn break or an operating error, since the yarn tension at the yarn tension sensor suddenly completely collapses.

The fault pattern illustrated in FIG. 3.3 defines the fault graph category C. The fault graph category C could represent, for example, a wear situation at the process assemblies of, for example, a cooling bar contacted by the yarn.

In the fault pattern illustrated in FIG. 3.4, the tolerance deviation of the measurement signal of the fault graph is at the lower limiting value. This indicates a short-term yarn tension loss. The associated fault pattern defines in this case the fault graph category D. A process disturbance during the bobbin change in the bobbin point 2 could be present here.

In the fault pattern illustrated in FIG. 3.5, a reoccurring exceeding of the measurement signal of the yarn tension in relation to the upper limiting value is measured. The associated fault pattern forms the fault graph category E in this case. The fault graph category E could be, for example, an uneven texturing of the yarn.

A specific process disturbance or a specific operating fault or a specific product fault is thus assigned to each of the fault graph categories A to E. The fault graph categories illustrated in FIGS. 3.1 to 3.5 are exemplary. In a yarn treatment process as shown in FIG. 1, a variety of fault graph categories can occur which are the result of a unique cause in the process.

In the diagnostic unit 18 illustrated in FIG. 2, the fault graph provided by the yarn tension analysis unit 19 is analyzed using the machine learning program inside the learning processor 20. For this purpose, the fault graph is analyzed with the aid of at least one, preferably multiple machine learning algorithms. At the end of the analysis, a classification into one of the already learned fault graph categories takes place. If this is a fault graph category which is not yet known in this case, a new fault category is provided and accommodated within the machine learning program of the learning processor.

To execute the operations, the learning processor comprises a neural network to be able to execute the machine learning algorithm. The diagnostic unit is thus fully autonomous to analyze the fault graphs and thus monitor the yarn tension and initiate corresponding measures to remedy disturbances.

In the exemplary embodiment according to FIG. 2, the present analysis of the fault graphs has resulted in an assignment to the fault graph category A. This fault graph category is visualized at the output unit 23, for example, by the fault pattern, so that an operator is informed and can possibly carry out actions themselves. Alternatively, however, a signal could be given directly to the machine control unit 16 by the learning processor 20. The learning processor 20 is therefore also connected to the machine control unit 16. Thus, for example, in the case of the fault graph category A, a premature bobbin change could be initiated in order not to include a knotted connection in the wound bobbin.

In the later course of the process, the diagnostic unit 18 is also capable of generating new, previously unknown fault categories. The diagnostic unit 18 thus represents a self-learning system by which an automated classification into various categories is performed. Each of the fault graph categories could represent a specific process disturbance in this case, so that the acquired fault graphs could automatically be assigned a disturbance parameter via the fault graph category. Rapid and unambiguous fault diagnoses in the texturing process could thus be executed by way of the relationship between fault graph category and disturbance parameter and automatically eliminated by corresponding reactions.

The invention claimed is:

1. A method for monitoring a yarn tension of a running yarn in a yarn treatment process, in which the yarn tension of the yarn is progressively measured, in which measurement signals of the yarn tension are compared to at least one limiting value of a permissible yarn tension and in which in the event of an impermissible tolerance deviation of the measurement signals, a short-term signal profile of the yarn tension is acquired as a fault graph, wherein the fault graph of the yarn tension is analyzed using a machine learning program, wherein the fault graph is assigned to a particular fault graph category that is either a known fault graph category or a new fault graph category, wherein the particular fault graph category is visualized at an output unit, and wherein after assignment of the fault graph to the particular fault graph category, the method includes automatically triggering a control command for a process change related to the particular fault graph category, the control command automatically initiating an intervention to address a fault in the yarn treatment process corresponding to the particular fault graph category and to remedy a disturbance.

2. The method as claimed in claim 1, wherein the fault graph categories are each specified by a fault pattern of one of the fault graphs and/or a group of fault graphs.

3. The method as claimed in claim 1, wherein a specific process disturbance and/or a specific operating fault and/or a specific disturbance parameter and/or a specific product fault is/are assigned to each of the fault graph categories.

4. The method as claimed in claim 1, wherein the analysis of the fault graphs is executed by at least one machine learning algorithm of the machine learning program.

5. The method as claimed in claim 4, wherein at least one of the fault graph categories is defined solely by the machine learning algorithm from analyzed fault graphs.

6. A method as in claim 1, wherein the control command automatically initiating the intervention includes initiating a direct intervention into the yarn treatment process to remedy the disturbance.

7. A method as in claim 1, wherein the control command automatically initiating the intervention includes initiating an operator intervention by an operator into the yarn treatment process to remedy the disturbance.

8. A method as in claim 1, wherein comparing the measurement signals of the yarn tension to at least one limiting value of a permissible yarn tension includes comparing the measurement signals of the yarn tension to an upper limiting value and a lower limiting value of a permissible yarn tension and wherein a short-term exceeding of the upper limiting value is assigned to a fault graph category that refers to a knot overflow.

9. A method as in claim 8, wherein automatically initiating the intervention to address the fault in the yarn treatment process includes changing a bobbin.

10. A method as in claim 1, wherein automatically initiating the intervention to address the fault in the yarn treatment process includes changing a bobbin.

11. A device for monitoring a yarn tension of a running yarn in a yarn treatment process, comprising:
a yarn tension measuring unit having a yarn tension sensor and having a measurement signal pickup, and
a yarn tension analysis unit having a fault graph generator,
wherein the yarn tension analysis unit interacts with a diagnostic unit in such a way that a fault graph is analyzable using a machine learning program,
wherein the fault graph is assigned by the device to a particular fault graph category that is either a known fault graph category or a new fault graph category,
wherein the particular fault graph category is visualized at an output unity, and
wherein after assignment of the fault graph to the particular fault graph category, the device is configured to automatically trigger a control command for a process change related to the particular fault graph category, the device configured to respond to the control command automatically by initiating an intervention to address a fault in the yarn treatment process corresponding to the particular fault graph category and to remedy a disturbance.

12. The device as claimed in claim 11, wherein the diagnostic unit comprises a storage unit and a programmable learning processor for executing the machine learning program.

13. The device as claimed in claim 12, wherein the learning processor is coupled to an input unit, by which one or more ascertained fault graphs can be input.

14. The device as claimed in claim 12, wherein the learning processor is coupled to the output unit, by which an assignment of the analyzed fault graphs to one of the fault graph categories can be visualized.

15. The device as claimed in claim 12, wherein the learning processor comprises a neural network for executing the machine learning program.

16. The device as claimed in claim 11, wherein the diagnostic unit is connected to a machine control unit, by which the control command for the process change is executable.

17. A method for monitoring a yarn tension of a running yarn in a yarn treatment process, the method comprising:
progressively measuring the yarn tension of the running yarn in the yarn treatment process to provide measurement signals identifying the yarn tension,
comparing the measurement signals to at least one limiting value of a permissible yarn tension to detect an event of an impermissible tolerance deviation of the measurement signals,
in response to the event of the impermissible tolerance deviation of the measurement signals, acquiring a short-term signal profile of the yarn tension as a fault graph of the yarn tension,
analyzing the fault graph of the yarn tension using a machine learning program,
based on analyzing the fault graph of the yarn tension, assigning the fault graph to a particular fault graph category that is either a known fault graph category and a new fault graph category, and
visualizing the particular fault graph category at an output unit, wherein the method further comprises,
after assigning the fault graph to the particular fault graph category, automatically triggering a control command for a process change related to the particular fault graph category, the control command automatically initiating an intervention to address a fault in the yarn treatment process corresponding to the particular fault graph category and to remedy a disturbance.

* * * * *